(12) United States Patent
Jiang et al.

(10) Patent No.: US 12,076,533 B2
(45) Date of Patent: Sep. 3, 2024

(54) CONTEXTUAL ADJUSTMENT OF INSULIN ABSORPTION CURVES

(71) Applicant: Medtronic MiniMed, Inc., Northridge, CA (US)

(72) Inventors: Boyi Jiang, Pasadena, CA (US); Yuxiang Zhong, Arcadia, CA (US); Pratik J. Agrawal, Porter Ranch, CA (US)

(73) Assignee: MEDTRONIC MINIMED, INC., Northridge (CA)

( * ) Notice: Subject to any disclaimer, the term of this patent is extended or adjusted under 35 U.S.C. 154(b) by 345 days.

(21) Appl. No.: 17/645,693

(22) Filed: Dec. 22, 2021

(65) Prior Publication Data

US 2022/0111144 A1     Apr. 14, 2022

Related U.S. Application Data

(63) Continuation of application No. 16/578,241, filed on Sep. 20, 2019, now Pat. No. 11,213,623.

(51) Int. Cl.
*A61M 5/172*     (2006.01)
*A61M 5/145*     (2006.01)
*G16H 10/60*     (2018.01)
*G16H 20/17*     (2018.01)

(52) U.S. Cl.
CPC ........ *A61M 5/1723* (2013.01); *A61M 5/1452* (2013.01); *G16H 10/60* (2018.01); *G16H 20/17* (2018.01); *A61M 2205/50* (2013.01); *A61M 2205/8206* (2013.01); *A61M 2230/201* (2013.01)

(58) Field of Classification Search
None
See application file for complete search history.

(56) References Cited

U.S. PATENT DOCUMENTS

| | | | |
|---|---|---|---|
| 4,562,751 A | 1/1986 | Nason et al. |
| 4,685,903 A | 8/1987 | Cable et al. |
| 4,755,173 A | 7/1988 | Konopka et al. |
| 5,080,653 A | 1/1992 | Voss et al. |
| 5,097,122 A | 3/1992 | Colman et al. |

(Continued)

FOREIGN PATENT DOCUMENTS

| | | |
|---|---|---|
| CN | 104756116 A | 7/2015 |
| CN | 104769595 A | 7/2015 |

(Continued)

OTHER PUBLICATIONS

International Search Report and Written Opinion from counterpart International Application No. PCT/US2020/050963, dated Dec. 1, 2020, 16 pp.

(Continued)

*Primary Examiner* — Manuel A Mendez
(74) *Attorney, Agent, or Firm* — Weaver Austin Villeneuve & Sampson LLP

(57) ABSTRACT

A processor-implemented method includes identifying a reference insulin absorption curve for a patient based on demographic data of the patient, identifying a contextual adjustment factor based on current contextual information for the patient, obtaining an adjusted insulin absorption curve based on the reference insulin absorption curve and the contextual adjustment factor, and causing insulin delivery to the patient based on the adjusted insulin absorption curve.

20 Claims, 7 Drawing Sheets

(56) References Cited

U.S. PATENT DOCUMENTS

| | | |
|---|---|---|
| 5,391,250 A | 2/1995 | Cheney, II et al. |
| 5,485,408 A | 1/1996 | Blomquist |
| 5,505,709 A | 4/1996 | Funderburk et al. |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,088,608 A | 7/2000 | Schulman et al. |
| 6,119,028 A | 9/2000 | Schulman et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,485,465 B2 | 11/2002 | Moberg et al. |
| 6,544,212 B2 | 4/2003 | Galley et al. |
| 6,554,798 B1 | 4/2003 | Mann et al. |
| 6,558,320 B1 | 5/2003 | Causey et al. |
| 6,558,351 B1 | 5/2003 | Steil et al. |
| 6,589,229 B1 | 7/2003 | Connelly et al. |
| 6,591,876 B2 | 7/2003 | Safabash |
| 6,641,533 B2 | 11/2003 | Causey et al. |
| 6,659,980 B2 | 12/2003 | Moberg et al. |
| 6,736,797 B1 | 5/2004 | Larsen et al. |
| 6,740,072 B2 | 5/2004 | Starkweather et al. |
| 6,749,587 B2 | 6/2004 | Flaherty |
| 6,752,787 B1 | 6/2004 | Causey et al. |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,817,990 B2 | 11/2004 | Yap et al. |
| 6,827,702 B2 | 12/2004 | Lebel et al. |
| 6,932,584 B2 | 8/2005 | Gray et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,323,142 B2 | 1/2008 | Pendo et al. |
| 7,399,277 B2 | 7/2008 | Saidara et al. |
| 7,402,153 B2 | 7/2008 | Steil et al. |
| 7,442,186 B2 | 10/2008 | Blomquist |
| 7,602,310 B2 | 10/2009 | Mann et al. |
| 7,621,893 B2 | 11/2009 | Moberg et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 8,474,332 B2 | 7/2013 | Bente et al. |
| 8,674,288 B2 | 3/2014 | Hanson et al. |
| 2006/0031094 A1 | 2/2006 | Cohen et al. |
| 2007/0123819 A1 | 5/2007 | Mernoe et al. |
| 2008/0172028 A1 | 7/2008 | Blomquist et al. |
| 2010/0160861 A1 | 6/2010 | Causey, III et al. |
| 2013/0041343 A1 | 2/2013 | Toumazou et al. |
| 2013/0338630 A1 | 12/2013 | Agrawal et al. |
| 2014/0066889 A1 | 3/2014 | Grosman et al. |
| 2016/0279336 A1 | 9/2016 | Roy |
| 2017/0049963 A1 | 2/2017 | Varsavsky et al. |
| 2018/0169334 A1 | 6/2018 | Grosman et al. |
| 2019/0252079 A1 | 8/2019 | Constantin et al. |

FOREIGN PATENT DOCUMENTS

| | | |
|---|---|---|
| CN | 105339943 A | 2/2016 |
| CN | 107073207 A | 8/2017 |
| CN | 107135644 A | 9/2017 |
| CN | 110191731 A | 8/2019 |
| TW | 201900229 A | 1/2019 |

OTHER PUBLICATIONS

Prosecution History from U.S. Appl. No. 16/578,241, now issued U.S. Pat. No. 11,213,623, dated Aug. 27, 2021, 8 pp.
CN Office Action dated Mar. 19, 2024 in CN Application No. 202080065614.1, with English Translation [C00019131CN01].

CONTEXTUAL ADJUSTMENT OF INSULIN ABSORPTION CURVES

This application is a continuation of U.S. application Ser. No. 16/578,241, filed Sep. 20, 2019, the entire content of which is incorporated herein by reference.

TECHNICAL FIELD

Embodiments of the subject matter described herein relate generally to medical devices, and more particularly, embodiments of the subject matter relate to automatically adapting operations of a fluid infusion device in a personalized manner.

BACKGROUND

Infusion pump devices and systems are relatively well known in the medical arts, for use in delivering or dispensing an agent, such as insulin or another prescribed medication, to a patient. A typical infusion pump includes a pump drive system which typically includes a small motor and drive train components that convert rotational motor motion to a translational displacement of a plunger (or stopper) in a reservoir that delivers medication from the reservoir to the body of a user via a fluid path created between the reservoir and the body of a user. Use of infusion pump therapy has been increasing, especially for delivering insulin for diabetics.

Managing a diabetic's blood glucose level is also complicated by the user's consumption of meals or carbohydrates. Often, a user manually administers a bolus of insulin at or around meal time to mitigate postprandial hyperglycemia. To effectively mitigate postprandial hyperglycemia while also avoiding postprandial hypoglycemia, the user is often required to estimate the amount of carbohydrates being consumed, with that amount of carbohydrates then being utilized to determine the appropriate bolus dosage. However, regulating blood glucose level is also complicated by variations in the response time for the type of insulin being used along with each user's individual insulin response. Furthermore, a user's daily activities and experiences may cause that user's insulin response to vary throughout the course of a day or from one day to the next. Thus, it is desirable to account for the anticipated variations or fluctuations in the user's insulin response caused by the user's activities or other condition(s) experienced by the user.

BRIEF SUMMARY

Infusion devices, infusion systems, and related operating methods are provided. In some examples, the disclosure describes a processor-implemented method comprising: identifying a reference insulin absorption curve for a patient based on demographic data of the patient; identifying a contextual adjustment factor based on current contextual information for the patient; obtaining an adjusted insulin absorption curve based on the reference insulin absorption curve and the contextual adjustment factor; and causing insulin delivery to the patient based on the adjusted insulin absorption curve.

In some examples, the disclosure describes a system comprising: one or more processors; and one or more processor-readable storage media storing instructions which, when executed by the one or more processors, cause performance of: identifying a reference insulin absorption curve for a patient based on demographic data of the patient; identifying a contextual adjustment factor based on current contextual information for the patient; obtaining an adjusted insulin absorption curve based on the reference insulin absorption curve and the contextual adjustment factor; and causing insulin delivery to the patient based on the adjusted insulin absorption curve.

In some examples, the disclosure describes one or more processor-readable storage media storing instructions which, when executed by one or more processors, cause performance of: identifying a reference insulin absorption curve for a patient based on demographic data of the patient; identifying a contextual adjustment factor based on current contextual information for the patient; obtaining an adjusted insulin absorption curve based on the reference insulin absorption curve and the contextual adjustment factor; and causing insulin delivery to the patient based on the adjusted insulin absorption curve.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and are not necessarily drawn to scale.

DETAILED DESCRIPTION

Figure 1:
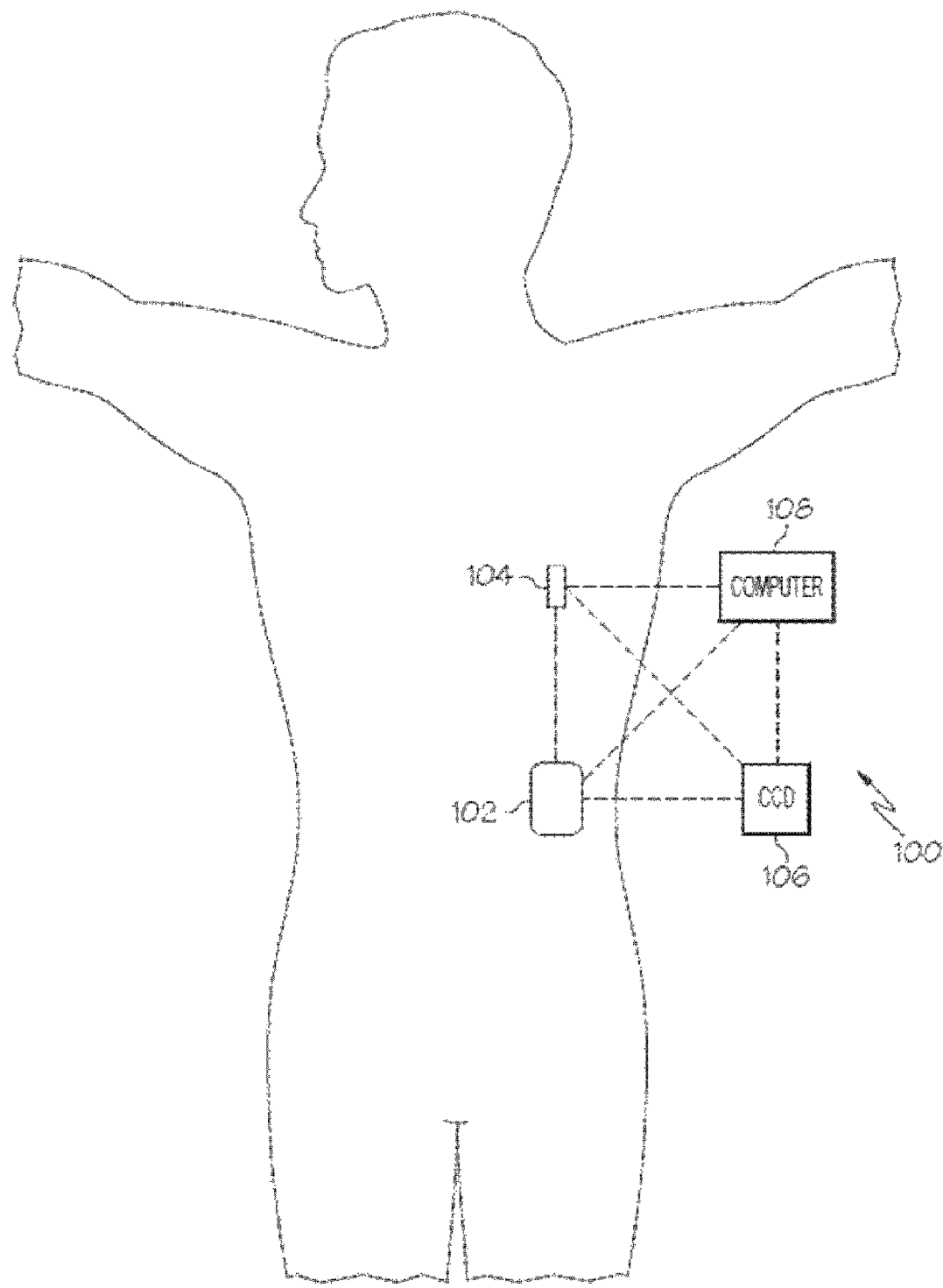
FIG. 1 depicts an exemplary embodiment of an infusion system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Exemplary embodiments of the subject matter described herein are implemented in conjunction with medical devices, such as portable electronic medical devices. Although many different applications are possible, the following description focuses on embodiments that incorporate a fluid infusion device (or infusion pump) as part of an infusion system deployment. That said, the subject matter described herein is not limited to infusion devices (or any particular configuration or realization thereof) and may be implemented in an equivalent manner in the context of multiple daily injection (MDI) therapy regimen or other medical devices, such as continuous glucose monitoring (CGM) devices, injection pens (e.g., smart injection pens), and the like. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos.: 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference.

Generally, a fluid infusion device includes a motor or other actuation arrangement that is operable to displace a plunger (or stopper) or other delivery mechanism to deliver a dosage of fluid, such as insulin, from a reservoir provided within the fluid infusion device to the body of a patient. Dosage commands that govern operation of the motor may be generated in an automated manner in accordance with the delivery control scheme associated with a particular operating mode, and the dosage commands may be generated in a manner that is influenced by a current (or most recent) measurement of a physiological condition in the body of the user. For example, in a closed-loop operating mode, dosage commands may be generated based on a difference between a current (or most recent) measurement of the interstitial fluid glucose level in the body of the user and a target (or reference) glucose value. In this regard, the rate of infusion may vary as the difference between a current measurement value and the target measurement value fluctuates. For purposes of explanation, the subject matter is described herein in the context of the infused fluid being insulin for regulating a glucose level of a user (or patient); however, it should be appreciated that many other fluids may be administered through infusion, and the subject matter described herein is not necessarily limited to use with insulin.

As described in greater detail below in the context of FIGS. 5-8, in one or more exemplary embodiments, bolus dosages are calculated or otherwise determined in a personalized, patient-specific manner using an insulin absorption curve (or insulin absorption rate), which corresponds to a decay curve that quantifies the remaining amount of insulin on board (IOB) (or residual insulin) that is yet to be metabolized with respect to time after subcutaneous injection. In exemplary embodiments, the insulin absorption curve (or alternatively, the time constants, decay factors, and/or other parameters characterizing the rate of metabolism) is not static, but rather is dynamically determined in real-time at the time of a bolus. Additionally, rather than relying on manual selection of a fixed insulin absorption curve (or rate), a reference insulin absorption curve for the patient is adjusted based on the current or recent contextual state of the patient, resulting in a personalized and contextually-adjusted insulin absorption curve that dynamically varies in response to changes in the patient's context substantially in real-time.

As described in greater detail below, the reference insulin absorption curve for the patient is determined using the patient's demographic data (e.g., the patient's age, gender, race, body mass index, height, weight, years on insulin therapy, income level, education level, profession, geographic region, and/or the like) to assign the patient to a cluster group of similar patients, with the reference insulin absorption curve for that patient cluster group being calculated, determined, or otherwise derived using historical data associated with patients assigned to that cluster group. A contextual adjustment factor is determined based on the current patient context, for example, by inputting or otherwise providing current or recent measurement values or other data for a number of contextual variables into a contextual adjustment model. An adjusted insulin absorption curve for the current patient context is then calculated as a function of the reference insulin absorption curve and the contextual adjustment factor.

In exemplary embodiments, a bolus wizard or similar feature of an infusion device control system utilizes the contextually-adjusted insulin absorption curve to estimate or otherwise determine the patient's insulin on board (IOB) at the time of the bolus and/or for a future time period (and the corresponding expected glycemic response to insulin absorption), which, in turn, is utilized to calculate or otherwise determine a bolus dosage of insulin to be delivered (e.g., by subtracting the current IOB from the calculated amount of insulin needed to compensate for the amount of carbohydrates determined from the patient's carbohydrate ratio). By utilizing an insulin absorption curve that better reflects the patient's anticipated glycemic response, the effectiveness of the resulting bolus dosage mitigating subsequent hyperglycemia, hypoglycemia, or other glycemic excursions or abnormalities is improved. Additionally, the automated selection of the insulin absorption curve reduces the patient burden and the likelihood of manual errors while also improving therapy effectiveness.

Infusion System Overview

FIG. 1 depicts one exemplary embodiment of an infusion system 100 that includes, without limitation, a fluid infusion device (or infusion pump) 102, a sensing arrangement 104, a command control device (CCD) 106, and a computer 108. The components of an infusion system 100 may be realized using different platforms, designs, and configurations, and the embodiment shown in FIG. 1 is not exhaustive or limiting. In practice, the infusion device 102 and the sensing arrangement 104 are secured at desired locations on the body of a user (or patient), as illustrated in FIG. 1. In this regard, the locations at which the infusion device 102 and the sensing arrangement 104 are secured to the body of the user in FIG. 1 are provided only as a representative, non-limiting, example. The elements of the infusion system 100 may be similar to those described in U.S. Pat. No. 8,674,288, the subject matter of which is hereby incorporated by reference in its entirety.

In the illustrated embodiment of FIG. 1, the infusion device 102 is designed as a portable medical device suitable for infusing a fluid, a liquid, a gel, or other medicament into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like.

The sensing arrangement 104 generally represents the components of the infusion system 100 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 104 may include electronics and enzymes reactive to a biological condition, such as a blood glucose level, or the like, of the user, and provide data indicative of the blood glucose level to the infusion device 102, the CCD 106 and/or the computer 108. For example, the infusion device 102, the CCD 106 and/or the computer 108 may include a display for presenting information or data to the user based on the sensor data received from the sensing arrangement 104, such as, for example, a current glucose level of the user, a graph or chart of the user's glucose level versus time, device status indicators, alert messages, or the like. In other embodiments, the infusion device 102, the CCD 106 and/or the computer 108 may include electronics and software that are configured to analyze sensor data and operate the infusion device 102 to deliver fluid to the body of the user based on the sensor data and/or preprogrammed delivery routines. Thus, in exemplary embodiments, one or more of the infusion device 102, the sensing arrangement 104, the CCD 106, and/or the computer 108 includes a transmitter, a receiver, and/or other transceiver electronics that allow for communication with other components of the infusion system 100, so that the sensing arrangement 104 may transmit sensor data or monitor data to one or more of the infusion device 102, the CCD 106 and/or the computer 108.

Still referring to FIG. 1, in various embodiments, the sensing arrangement 104 may be secured to the body of the user or embedded in the body of the user at a location that is remote from the location at which the infusion device 102 is secured to the body of the user. In various other embodiments, the sensing arrangement 104 may be incorporated within the infusion device 102. In other embodiments, the sensing arrangement 104 may be separate and apart from the infusion device 102, and may be, for example, part of the CCD 106. In such embodiments, the sensing arrangement 104 may be configured to receive a biological sample, analyte, or the like, to measure a condition of the user.

In some embodiments, the CCD 106 and/or the computer 108 may include electronics and other components configured to perform processing, delivery routine storage, and to control the infusion device 102 in a manner that is influenced by sensor data measured by and/or received from the sensing arrangement 104. By including control functions in the CCD 106 and/or the computer 108, the infusion device 102 may be made with more simplified electronics. However, in other embodiments, the infusion device 102 may include all control functions, and may operate without the CCD 106 and/or the computer 108. In various embodiments, the CCD 106 may be a portable electronic device. In addition, in various embodiments, the infusion device 102 and/or the sensing arrangement 104 may be configured to transmit data to the CCD 106 and/or the computer 108 for display or processing of the data by the CCD 106 and/or the computer 108.

In some embodiments, the CCD 106 and/or the computer 108 may provide information to the user that facilitates the user's subsequent use of the infusion device 102. For example, the CCD 106 may provide information to the user to allow the user to determine the rate or dose of medication to be administered into the user's body. In other embodiments, the CCD 106 may provide information to the infusion device 102 to autonomously control the rate or dose of medication administered into the body of the user. In some embodiments, the sensing arrangement 104 may be integrated into the CCD 106. Such embodiments may allow the user to monitor a condition by providing, for example, a sample of his or her blood to the sensing arrangement 104 to assess his or her condition. In some embodiments, the sensing arrangement 104 and the CCD 106 may be used for determining glucose levels in the blood and/or body fluids of the user without the use of, or necessity of, a wire or cable connection between the infusion device 102 and the sensing arrangement 104 and/or the CCD 106.

In some embodiments, the sensing arrangement 104 and/or the infusion device 102 are cooperatively configured to utilize a closed-loop system for delivering fluid to the user. Examples of sensing devices and/or infusion pumps utilizing closed-loop systems may be found at, but are not limited to, the following U.S. Pat. Nos.: 6,088,608, 6,119,028, 6,589,229, 6,740,072, 6,827,702, 7,323,142, and 7,402,153 or United States Patent Application Publication No. 2014/0066889, all of which are incorporated herein by reference in their entirety. In such embodiments, the sensing arrangement 104 is configured to sense or measure a condition of the user, such as, blood glucose level or the like. The infusion device 102 is configured to deliver fluid in response to the condition sensed by the sensing arrangement 104. In turn, the sensing arrangement 104 continues to sense or otherwise quantify a current condition of the user, thereby allowing the infusion device 102 to deliver fluid continuously in response to the condition currently (or most recently) sensed by the sensing arrangement 104 indefinitely. In some embodiments, the sensing arrangement 104 and/or the infusion device 102 may be configured to utilize the closed-loop system only for a portion of the day, for example only when the user is asleep or awake.

Figure 2:
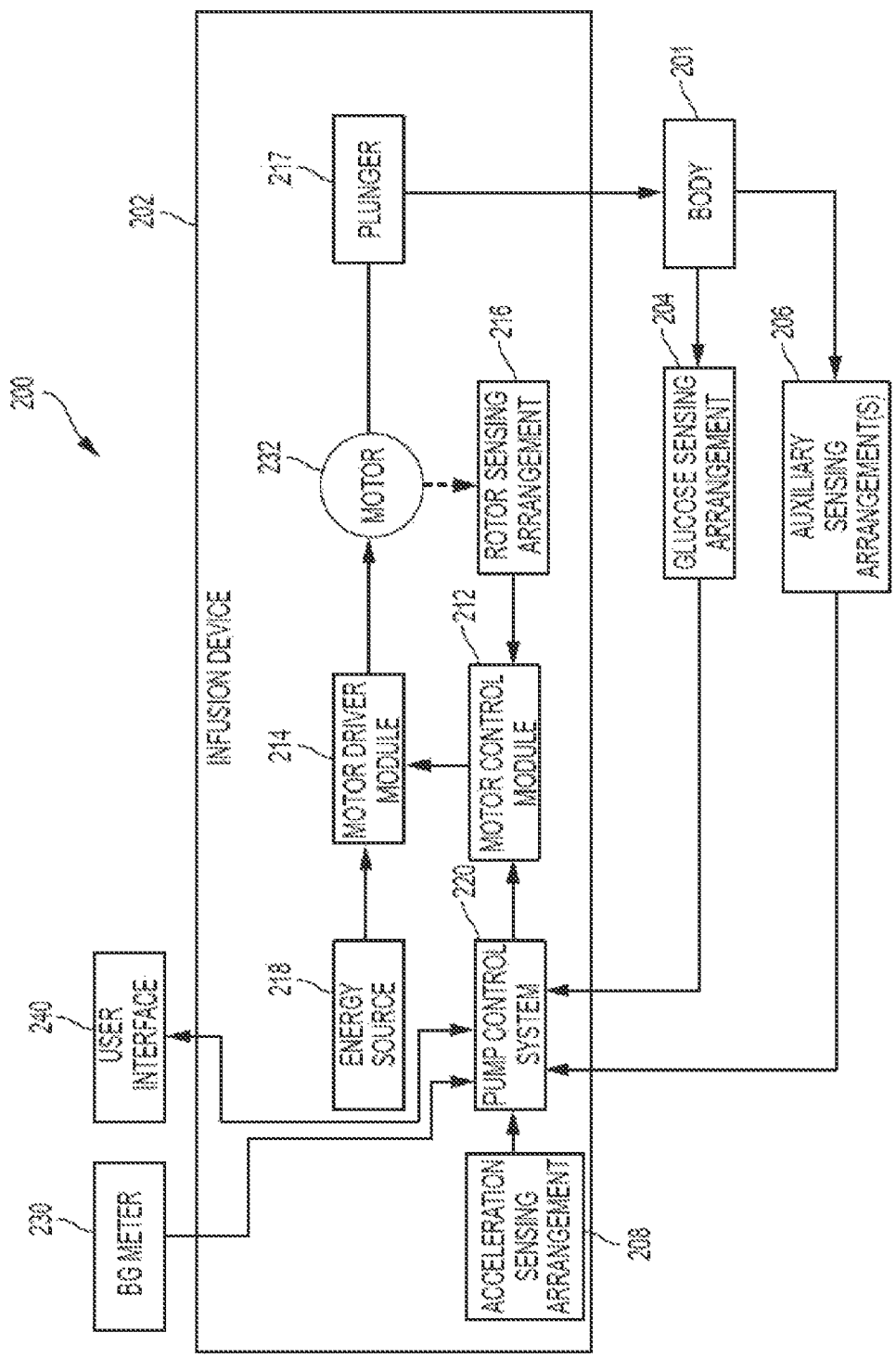
FIG. 2 is a block diagram of an exemplary control system suitable for use with a fluid infusion device in one or more embodiments.

FIG. 2 depicts an exemplary embodiment of a control system 200 suitable for use with an infusion device 202, such as the infusion device 102 described above. The control system 200 is capable of controlling or otherwise regulating a physiological condition in the body 201 of a patient to a desired (or target) value or otherwise maintain the condition within a range of acceptable values in an automated or autonomous manner. In one or more exemplary embodiments, the condition being regulated is sensed, detected, measured or otherwise quantified by a sensing arrangement 204 (e.g., sensing arrangement 104) communicatively coupled to the infusion device 202. However, it should be noted that in alternative embodiments, the condition being regulated by the control system 200 may be correlative to the measured values obtained by the sensing arrangement 204. That said, for clarity and purposes of explanation, the subject matter may be described herein in the context of the sensing arrangement 204 being realized as a glucose sensing arrangement that senses, detects, measures or otherwise quantifies the patient's glucose level, which is being regulated in the body 201 of the patient by the control system 200.

In exemplary embodiments, the sensing arrangement 204 includes one or more interstitial glucose sensing elements that generate or otherwise output electrical signals (alternatively referred to herein as measurement signals) having a signal characteristic that is correlative to, influenced by, or otherwise indicative of the relative interstitial fluid glucose level in the body 201 of the patient. The output electrical signals are filtered or otherwise processed to obtain a measurement value indicative of the patient's interstitial fluid glucose level. In exemplary embodiments, a blood glucose meter 230, such as a finger stick device, is utilized to directly sense, detect, measure or otherwise quantify the blood glucose in the body 201 of the patient. In this regard, the blood glucose meter 230 outputs or otherwise provides a measured blood glucose value that may be utilized as a reference measurement for calibrating the sensing arrangement 204 and converting a measurement value indicative of the patient's interstitial fluid glucose level into a corresponding calibrated blood glucose value. For purposes of explanation, the calibrated blood glucose value calculated based on the electrical signals output by the sensing element(s) of the sensing arrangement 204 may alternatively be referred to herein as the sensor glucose value, the sensed glucose value, or variants thereof.

In the illustrated embodiment, the control system 200 also includes one or more additional sensing arrangements 206, 208 configured to sense, detect, measure or otherwise quantify a characteristic of the body 201 of the patient that is indicative of a condition in the body 201 of the patient. In this regard, in addition to the glucose sensing arrangement 204, one or more auxiliary sensing arrangements 206 may be worn, carried, or otherwise associated with the body 201 of the patient to measure characteristics or conditions of the patient (or the patient's activity) that may influence the patient's glucose levels or insulin sensitivity. For example, a heart rate sensing arrangement 206 could be worn on or otherwise associated with the patient's body 201 to sense, detect, measure or otherwise quantify the patient's heart rate, which, in turn, may be indicative of exercise (and the intensity thereof) that is likely to influence the patient's glucose levels or insulin response in the body 201. In yet another embodiment, another invasive, interstitial, or subcutaneous sensing arrangement 206 may be inserted into the body 201 of the patient to obtain measurements of another physiological condition that may be indicative of exercise (and the intensity thereof), such as, for example, a lactate sensor, a ketone sensor, or the like. Depending on the embodiment, the auxiliary sensing arrangement(s) 206 could be realized as a standalone component worn by the patient, or alternatively, the auxiliary sensing arrangement(s) 206 may be integrated with the infusion device 202 or the glucose sensing arrangement 204.

The illustrated control system 200 also includes an acceleration sensing arrangement 208 (or accelerometer) that may be worn on or otherwise associated with the patient's body 201 to sense, detect, measure or otherwise quantify an acceleration of the patient's body 201, which, in turn, may be indicative of exercise or some other condition in the body 201 that is likely to influence the patient's insulin response. While the acceleration sensing arrangement 208 is depicted as being integrated into the infusion device 202 in FIG. 2, in alternative embodiments, the acceleration sensing arrangement 208 may be integrated with another sensing arrangement 204, 206 on the body 201 of the patient, or the acceleration sensing arrangement 208 may be realized as a separate standalone component that is worn by the patient.

In some embodiments, the infusion device 202 (or the control system 200) may also include one or more environmental sensing arrangements to sense, detect, measure or otherwise quantify the current operating environment around the infusion device 202. In this regard, the environmental sensing arrangements may include one or more of a temperature sensing arrangement (or thermometer), a humidity sensing arrangement, a pressure sensing arrangement (or barometer), and/or the like. Additionally, the infusion device 202 (or the control system 200) may also include a position sensing arrangement to sense, detect, measure or otherwise quantify the current geographic location of the infusion device 202, such as, for example, a global positioning system (GPS) receiver. Again, it should be noted that such sensing arrangements could be integrated into the infusion device 202, integrated with other components, or realized as separate standalone components that are worn or carried by the patient.

In the illustrated embodiment, the pump control system 220 generally represents the electronics and other components of the infusion device 202 that control operation of the fluid infusion device 202 according to a desired infusion delivery program in a manner that is influenced by the sensed glucose value indicating the current glucose level in the body 201 of the patient. For example, to support a closed-loop operating mode, the pump control system 220 maintains, receives, or otherwise obtains a target or commanded glucose value, and automatically generates or otherwise determines dosage commands for operating an actuation arrangement, such as a motor 232, to displace the plunger 217 and deliver insulin to the body 201 of the patient based on the difference between the sensed glucose value and the target glucose value. In other operating modes, the pump control system 220 may generate or otherwise determine dosage commands configured to maintain the sensed glucose value below an upper glucose limit, above a lower glucose limit, or otherwise within a desired range of glucose values. In practice, the infusion device 202 may store or otherwise maintain the target value, upper and/or lower glucose limit(s), insulin delivery limit(s), and/or other glucose threshold value(s) in a data storage element accessible to the pump control system 220. As described in greater detail, in one or more exemplary embodiments, the pump control system 220 automatically adjusts or adapts one or more parameters or other control information used to generate commands for operating the motor 232 in a manner that accounts for a likely change in the patient's glucose level or insulin response resulting from a meal, exercise, or other activity.

Still referring to FIG. 2, the target glucose value and other threshold glucose values utilized by the pump control system 220 may be received from an external component (e.g., CCD 106 and/or computing device 108) or be input by a patient via a user interface element 240 associated with the infusion device 202. In practice, the one or more user interface element(s) 240 associated with the infusion device 202 typically include at least one input user interface element, such as, for example, a button, a keypad, a keyboard, a knob, a joystick, a mouse, a touch panel, a touchscreen, a microphone or another audio input device, and/or the like. Additionally, the one or more user interface element(s) 240 include at least one output user interface element, such as, for example, a display element (e.g., a light-emitting diode or the like), a display device (e.g., a liquid crystal display or the like), a speaker or another audio output device, a haptic feedback device, or the like, for providing notifications or other information to the patient. It should be noted that although FIG. 2 depicts the user interface element(s) 240 as being separate from the infusion device 202, in practice, one or more of the user interface element(s) 240 may be integrated with the infusion device 202. Furthermore, in some embodiments, one or more user interface element(s) 240 are integrated with the sensing arrangement 204 in addition to and/or in alternative to the user interface element(s) 240 integrated with the infusion device 202. The user interface element(s) 240 may be manipulated by the patient to operate the infusion device 202 to deliver correction boluses, adjust target and/or threshold values, modify the delivery control scheme or operating mode, and the like, as desired.

Still referring to FIG. 2, in the illustrated embodiment, the infusion device 202 includes a motor control module 212 coupled to a motor 232 that is operable to displace a plunger 217 in a reservoir and provide a desired amount of fluid to the body 201 of a patient. In this regard, displacement of the plunger 217 results in the delivery of a fluid, such as insulin, that is capable of influencing the patient's physiological condition to the body 201 of the patient via a fluid delivery path (e.g., via tubing of an infusion set). A motor driver module 214 is coupled between an energy source 218 and the motor 232. The motor control module 212 is coupled to the motor driver module 214, and the motor control module 212 generates or otherwise provides command signals that operate the motor driver module 214 to provide current (or power) from the energy source 218 to the motor 232 to displace the plunger 217 in response to receiving, from a pump control system 220, a dosage command indicative of the desired amount of fluid to be delivered.

In exemplary embodiments, the energy source 218 is realized as a battery housed within the infusion device 202 that provides direct current (DC) power. In this regard, the motor driver module 214 generally represents the combination of circuitry, hardware and/or other electrical components configured to convert or otherwise transfer DC power provided by the energy source 218 into alternating electrical signals applied to respective phases of the stator windings of the motor 232 that result in current flowing through the stator windings that generates a stator magnetic field and causes the rotor of the motor 232 to rotate. The motor control module 212 is configured to receive or otherwise obtain a commanded dosage from the pump control system 220, convert the commanded dosage to a commanded translational displacement of the plunger 217, and command, signal, or otherwise operate the motor driver module 214 to cause the rotor of the motor 232 to rotate by an amount that produces the commanded translational displacement of the plunger 217. For example, the motor control module 212 may determine an amount of rotation of the rotor required to produce translational displacement of the plunger 217 that achieves the commanded dosage received from the pump control system 220. Based on the current rotational position (or orientation) of the rotor with respect to the stator that is indicated by the output of the rotor sensing arrangement 216, the motor control module 212 determines the appropriate sequence of alternating electrical signals to be applied to the respective phases of the stator windings that should rotate the rotor by the determined amount of rotation from its current position (or orientation). In embodiments where the motor 232 is realized as a BLDC motor, the alternating electrical signals commutate the respective phases of the stator windings at the appropriate orientation of the rotor magnetic poles with respect to the stator and in the appropriate order to provide a rotating stator magnetic field that rotates the rotor in the desired direction. Thereafter, the motor control module 212 operates the motor driver module 214 to apply the determined alternating electrical signals (e.g., the command signals) to the stator windings of the motor 232 to achieve the desired delivery of fluid to the patient.

When the motor control module 212 is operating the motor driver module 214, current flows from the energy source 218 through the stator windings of the motor 232 to produce a stator magnetic field that interacts with the rotor magnetic field. In some embodiments, after the motor control module 212 operates the motor driver module 214 and/or motor 232 to achieve the commanded dosage, the motor control module 212 ceases operating the motor driver module 214 and/or motor 232 until a subsequent dosage command is received. In this regard, the motor driver module 214 and the motor 232 enter an idle state during which the motor driver module 214 effectively disconnects or isolates the stator windings of the motor 232 from the energy source 218. In other words, current does not flow from the energy source 218 through the stator windings of the motor 232 when the motor 232 is idle, and thus, the motor 232 does not consume power from the energy source 218 in the idle state, thereby improving efficiency.

Depending on the embodiment, the motor control module 212 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In exemplary embodiments, the motor control module 212 includes or otherwise accesses a data storage element or memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by the motor control module 212. The computer-executable programming instructions, when read and executed by the motor control module 212, cause the motor control module 212 to perform or otherwise support the tasks, operations, functions, and processes described herein.

It should be appreciated that FIG. 2 is a simplified representation of the infusion device 202 for purposes of explanation and is not intended to limit the subject matter described herein in any way. In this regard, depending on the embodiment, some features and/or functionality of the sensing arrangement 204 may implemented by or otherwise integrated into the pump control system 220, or vice versa. Similarly, in practice, the features and/or functionality of the motor control module 212 may implemented by or otherwise integrated into the pump control system 220, or vice versa. Furthermore, the features and/or functionality of the pump control system 220 may be implemented by control electronics located in the fluid infusion device 202, while in alternative embodiments, the pump control system 220 may be implemented by a remote computing device that is physically distinct and/or separate from the infusion device 202, such as, for example, the CCD 106 or the computing device 108.

Figure 3:
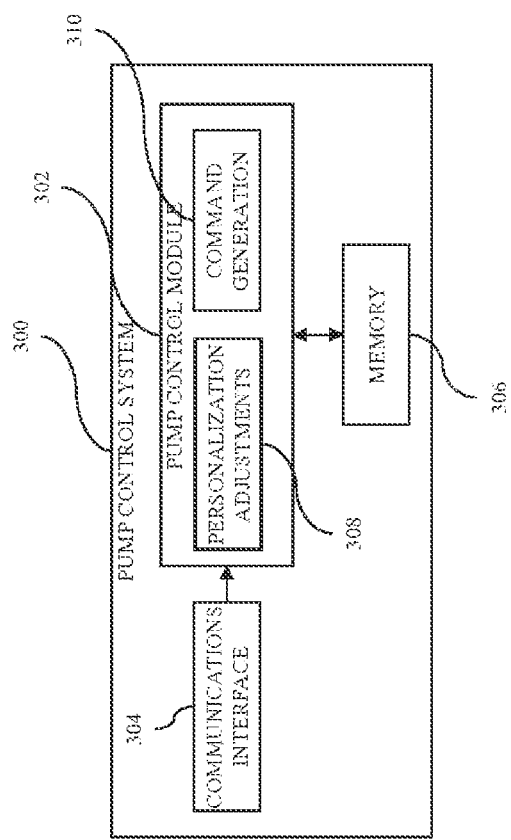
FIG. 3 is a block diagram of an exemplary pump control system suitable for use in the infusion device in the control system of FIG. 2 in one or more embodiments.

FIG. 3 depicts an exemplary embodiment of a pump control system 300 suitable for use as the pump control system 220 in FIG. 2 in accordance with one or more embodiments. The illustrated pump control system 300 includes, without limitation, a pump control module 302, a communications interface 304, and a data storage element (or memory) 306. The pump control module 302 is coupled to the communications interface 304 and the memory 306, and the pump control module 302 is suitably configured to support the operations, tasks, and/or processes described herein. In various embodiments, the pump control module 302 is also coupled to one or more user interface elements (e.g., user interface 240) for receiving user inputs (e.g., target glucose values or other glucose thresholds) and/or providing notifications, alerts, or other therapy information to the patient.

The communications interface 304 generally represents the hardware, circuitry, logic, firmware and/or other components of the pump control system 300 that are coupled to the pump control module 302 and configured to support communications between the pump control system 300 and the various sensing arrangements 204, 206, 208. In this regard, the communications interface 304 may include or otherwise be coupled to one or more transceiver modules capable of supporting wireless communications between the pump control system 220, 300 and the sensing arrangement(s) 204, 206, 208. For example, the communications interface 304 may be utilized to receive sensor measurement values or other measurement data from each sensing arrangement 204, 206, 208 in a control system 200. In other embodiments, the communications interface 304 may be configured to support wired communications to/from the sensing arrangement(s) 204, 206, 208. In various embodiments, the communications interface 304 may also support communications with another electronic device (e.g., CCD 106 and/or computer 108) in an infusion system (e.g., to upload sensor measurement values to a server or other computing device, receive control information from a server or other computing device, and the like).

The pump control module 302 generally represents the hardware, circuitry, logic, firmware and/or other component of the pump control system 300 that is coupled to the communications interface 304 and configured to determine dosage commands for operating the motor 232 to deliver fluid to the body 201 based on measurement data received from the sensing arrangements 204, 206, 208 and perform various additional tasks, operations, functions and/or operations described herein. For example, in exemplary embodiments, pump control module 302 implements or otherwise executes a command generation application 310 that supports one or more autonomous operating modes and calculates or otherwise determines dosage commands for operating the motor 232 of the infusion device 202 in an autonomous operating mode based at least in part on a current measurement value for a condition in the body 201 of the patient. For example, in a closed-loop operating mode, the command generation application 310 may determine a dosage command for operating the motor 232 to deliver insulin to the body 201 of the patient based at least in part on the current glucose measurement value most recently received from the sensing arrangement 204 to regulate the patient's blood glucose level to a target reference glucose value. Additionally, the command generation application 310 may generate dosage commands for boluses that are manually initiated or otherwise instructed by a patient via a user interface element.

In exemplary embodiments, the pump control module 302 also implements or otherwise executes a personalization application 308 that is cooperatively configured to interact with the command generation application 310 to support adjusting dosage commands or control information dictating the manner in which dosage commands are generated in a personalized, patient-specific manner. In this regard, in some embodiments, based on correlations between current or recent measurement data and the current operational context relative to historical data associated with the patient, the personalization application 308 may adjust or otherwise modify values for one or more parameters utilized by the command generation application 310 when determining dosage commands, for example, by modifying a parameter value at a register or location in memory 306 referenced by the command generation application 310. In yet other embodiments, the personalization application 308 may predict meals or other events or activities that are likely to be engaged in by the patient and output or otherwise provide an indication of the predicted patient behavior, which, in turn, may then be utilized to adjust the manner in which dosage commands are generated to regulate glucose in a manner that accounts for the patient's predicted behavior in a personalized manner. In some embodiments, the personalization application 308 may support automatically performing personalized adjustments of control parameters utilized by the command generation application 310.

Still referring to FIG. 3, depending on the embodiment, the pump control module 302 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In this regard, the steps of a method or algorithm described in connection with the embodiments disclosed herein may be embodied directly in hardware, in firmware, in a software module executed by the pump control module 302, or in any practical combination thereof. In exemplary embodiments, the pump control module 302 includes or otherwise accesses the data storage element or memory 306, which may be realized using any sort of non-transitory computer-readable medium capable of storing programming instructions for execution by the pump control module 302. The computer-executable programming instructions, when read and executed by the pump control module 302, cause the pump control module 302 to implement or otherwise generate the applications 308, 310 and perform tasks, operations, functions, and processes described herein.

It should be understood that FIG. 3 is a simplified representation of a pump control system 300 for purposes of explanation and is not intended to limit the subject matter described herein in any way. For example, in some embodiments, the features and/or functionality of the motor control module 212 may be implemented by or otherwise integrated into the pump control system 300 and/or the pump control module 302, for example, by the command generation application 310 converting the dosage command into a corresponding motor command, in which case, the separate motor control module 212 may be absent from an embodiment of the infusion device 202.

Figure 4:
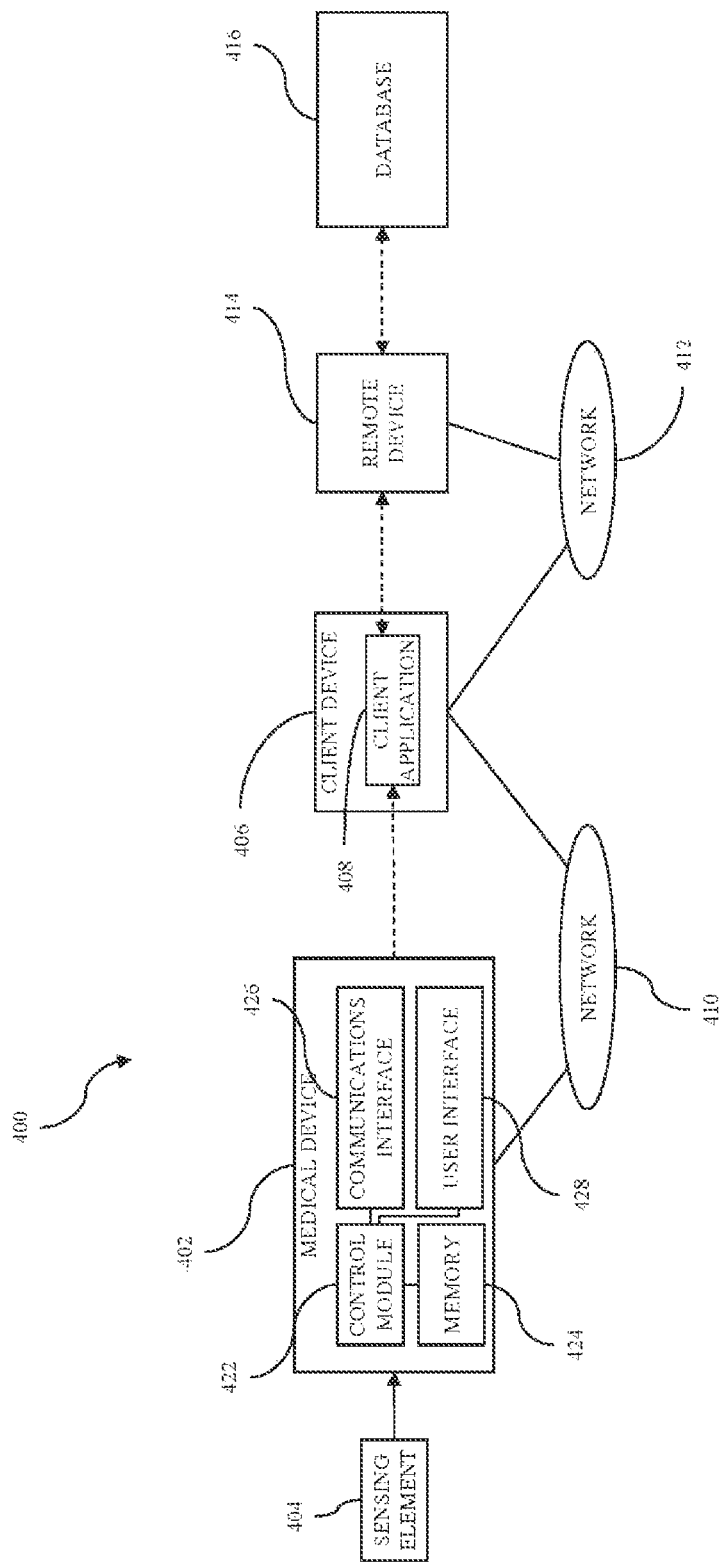
FIG. 4 is a block diagram of an exemplary patient monitoring system.

FIG. 4 depicts an exemplary embodiment of a patient monitoring system 400. The patient monitoring system 400 includes a medical device 402 that is communicatively coupled to a sensing element 404 that is inserted into the body of a patient or otherwise worn by the patient to obtain measurement data indicative of a physiological condition in the body of the patient, such as a sensed glucose level. In the illustrated embodiment, the medical device 402 is communicatively coupled to a client device 406 via a communications network 410, with the client device 406 being communicatively coupled to a remote device 414 via another communications network 412. In this regard, the client device 406 may function as an intermediary for uploading or otherwise providing measurement data from the medical device 402 to the remote device 414. It should be appreciated that FIG. 4 depicts a simplified representation of a patient monitoring system 400 for purposes of explanation and is not intended to limit the subject matter described herein in any way. For example, some embodiments may support direct communications between the medical device 402 and the remote device 414 via communications network 412.

In exemplary embodiments, the client device 406 is realized as a mobile phone, a smartphone, a tablet computer, or other similar mobile electronic device; however, in other embodiments, the client device 406 may be realized as any sort of electronic device capable of communicating with the medical device 402 via network 410, such as a laptop or notebook computer, a desktop computer, or the like. In exemplary embodiments, the network 410 is realized as a Bluetooth network, a ZigBee network, or another suitable personal area network. That said, in other embodiments, the network 410 could be realized as a wireless ad hoc network, a wireless local area network (WLAN), or local area network (LAN). The client device 406 includes or is coupled to a display device, such as a monitor, screen, or another conventional electronic display, capable of graphically presenting data and/or information pertaining to the physiological condition of the patient. The client device 406 also includes or is otherwise associated with a user input device, such as a keyboard, a mouse, a touchscreen, or the like, capable of receiving input data and/or other information from the user of the client device 406.

In some embodiments, a user, such as the patient, the patient's doctor or another healthcare provider, or the like, manipulates the client device 406 to execute a client application 408 that supports communicating with the medical device 402 via the network 410. In this regard, the client application 408 supports establishing a communications session with the medical device 402 on the network 410 and receiving data and/or information from the medical device 402 via the communications session. The medical device 402 may similarly execute or otherwise implement a corresponding application or process that supports establishing the communications session with the client application 408. The client application 408 generally represents a software module or another feature that is generated or otherwise implemented by the client device 406 to support the processes described herein. Accordingly, the client device 406 generally includes a processing system and a data storage element (or memory) capable of storing programming instructions for execution by the processing system, that, when read and executed, cause processing system to create, generate, or otherwise facilitate the client application 408 and perform or otherwise support the processes, tasks, operations, and/or functions described herein. Depending on the embodiment, the processing system may be implemented using any suitable processing system and/or device, such as, for example, one or more processors, central processing units (CPUs), controllers, microprocessors, microcontrollers, processing cores and/or other hardware computing resources configured to support the operation of the processing system described herein. Similarly, the data storage element or memory may be realized as a random-access memory (RAM), read only memory (ROM), flash memory, magnetic or optical mass storage, or any other suitable non-transitory short or long-term data storage or other computer-readable media, and/or any suitable combination thereof.

In one or more embodiments, the client device 406 and the medical device 402 establish an association (or pairing) with one another over the network 410 to support subsequently establishing a point-to-point communications session between the medical device 402 and the client device 406 via the network 410. For example, in accordance with one embodiment, the network 410 is realized as a Bluetooth network, wherein the medical device 402 and the client device 406 are paired with one another (e.g., by obtaining and storing network identification information for one another) by performing a discovery procedure or another suitable pairing procedure. The pairing information obtained during the discovery procedure allows either of the medical device 402 or the client device 406 to initiate the establishment of a secure communications session via the network 410.

In one or more exemplary embodiments, the client application 408 is also configured to store or otherwise maintain a network address and/or other identification information for the remote device 414 on the second network 412. In this regard, the second network 412 may be physically and/or logically distinct from the network 410, such as, for example, the Internet, a cellular network, a wide area network (WAN), or the like. The remote device 414 generally represents a server or other computing device configured to receive and analyze or otherwise monitor measurement data, event log data, and potentially other information obtained for the patient associated with the medical device 402. In exemplary embodiments, the remote device 414 is coupled to a database 416 configured to store or otherwise maintain data associated with individual patients. In practice, the remote device 414 may reside at a location that is physically distinct and/or separate from the medical device 402 and the client device 406, such as, for example, at a facility that is owned and/or operated by or otherwise affiliated with a manufacturer of the medical device 402. For purposes of explanation, but without limitation, the remote device 414 may alternatively be referred to herein as a server.

It should be noted that in some embodiments, some or all of the functionality and processing intelligence of the remote computing device 414 can reside at the medical device 402 and/or at other components or computing devices that are compatible with the patient monitoring system 400. In other words, the patient monitoring system 400 need not rely on a network-based or a cloud-based server arrangement as depicted in FIG. 4, although such a deployment might be the most efficient and economical implementation. These and other alternative arrangements are contemplated by this disclosure. To this end, some embodiments of the system 400 may include additional devices and components that serve as data sources, data processing units, and/or recommendation delivery mechanisms. For example, the system 400 may include any or all of the following elements, without limitation: computer devices or systems; patient monitors; healthcare provider systems; data communication devices; and the like.

Still referring to FIG. 4, the sensing element 404 generally represents the component of the patient monitoring system 400 that is configured to generate, produce, or otherwise output one or more electrical signals indicative of a physiological condition that is sensed, measured, or otherwise quantified by the sensing element 404. In this regard, the physiological condition of a patient influences a characteristic of the electrical signal output by the sensing element 404, such that the characteristic of the output signal corresponds to or is otherwise correlative to the physiological condition that the sensing element 404 is sensitive to. In exemplary embodiments, the sensing element 404 is realized as an interstitial glucose sensing element inserted at a location on the body of the patient that generates an output electrical signal having a current (or voltage) associated therewith that is correlative to the interstitial fluid glucose level that is sensed or otherwise measured in the body of the patient by the sensing element 404.

The medical device 402 generally represents the component of the patient monitoring system 400 that is communicatively coupled to the output of the sensing element 404 to receive or otherwise obtain the measurement data samples from the sensing element 404 (e.g., the measured glucose and characteristic impedance values), store or otherwise maintain the measurement data samples, and upload or otherwise transmit the measurement data to the server 414 via the client device 406. In one or more embodiments, the medical device 402 is realized as an infusion device 102, 202 configured to deliver a fluid, such as insulin, to the body of the patient. That said, in other embodiments, the medical device 402 could be a standalone sensing or monitoring device separate and independent from an infusion device (e.g., sensing arrangement 104, 204), such as, for example, a continuous glucose monitor (CGM), an interstitial glucose sensing arrangement, or similar device. It should be noted that although FIG. 4 depicts the medical device 402 and the sensing element 404 as separate components, in practice, the medical device 402 and the sensing element 404 may be integrated or otherwise combined to provide a unitary device that can be worn by the patient.

In exemplary embodiments, the medical device 402 includes a control module 422, a data storage element 424 (or memory), a communications interface 426, and a user interface 428. The user interface 428 generally represents the input user interface element(s) and/or output user interface element(s) associated with the medical device 402 (e.g., one or more user interface elements 240). The control module 422 generally represents the hardware, circuitry, logic, firmware and/or other component(s) of the medical device 402 that is coupled to the sensing element 404 to receive the electrical signals output by the sensing element 404 and perform or otherwise support various additional tasks, operations, functions and/or processes described herein. Depending on the embodiment, the control module 422 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In some embodiments, the control module 422 includes an analog-to-digital converter (ADC) or another similar sampling arrangement that samples or otherwise converts an output electrical signal received from the sensing element 404 into corresponding digital measurement data value. In other embodiments, the sensing element 404 may incorporate an ADC and output a digital measurement value.

The communications interface 426 generally represents the hardware, circuitry, logic, firmware and/or other components of the medical device 402 that are coupled to the control module 422 for outputting data and/or information from/to the medical device 402 to/from the client device 406. For example, the communications interface 426 may include or otherwise be coupled to one or more transceiver modules capable of supporting wireless communications between the medical device 402 and the client device 406. In exemplary embodiments, the communications interface 426 is realized as a Bluetooth transceiver or adapter configured to support Bluetooth Low Energy (BLE) communications.

In exemplary embodiments, the remote device 414 receives, from the client device 406, measurement data values associated with a particular patient (e.g., sensor glucose measurements, acceleration measurements, and the like) that were obtained using the sensing element 404, and the remote device 414 stores or otherwise maintains the historical measurement data in the database 416 in association with the patient (e.g., using one or more unique patient identifiers). Additionally, the remote device 414 may also receive, from or via the client device 406, meal data or other event log data that may be input or otherwise provided by the patient (e.g., via client application 408) and store or otherwise maintain historical meal data and other historical event or activity data associated with the patient in the database 416. In this regard, the meal data include, for example, a time or timestamp associated with a particular meal event, a meal type or other information indicative of the content or nutritional characteristics of the meal, and an indication of the size associated with the meal. In exemplary embodiments, the remote device 414 also receives historical fluid delivery data corresponding to basal or bolus dosages of fluid delivered to the patient by an infusion device 102, 202. For example, the client application 408 may communicate with an infusion device 102, 202 to obtain insulin delivery dosage amounts and corresponding timestamps from the infusion device 102, 202, and then upload the insulin delivery data to the remote device 414 for storage in association with the particular patient. The remote device 414 may also receive geolocation data and potentially other contextual data associated with a device 402, 406 from the client device 406 and/or client application 408, and store or otherwise maintain the historical operational context data in association with the particular patient. In this regard, one or more of the devices 402, 406 may include a global positioning system (GPS) receiver or similar modules, components or circuitry capable of outputting or otherwise providing data characterizing the geographic location of the respective device 402, 406 in real-time.

Personalized Bolus Process

In exemplary embodiments, an infusion device (or a control system associated therewith) is capable of automatically determining a bolus amount in a personalized manner using an insulin absorption metric that is personalized to account for the patient's demographic data and dynamically adjusted to reflect the current operating context or state of the patient. The resulting personalized and contextually adjusted insulin absorption metric accounts for absorption variabilities to improve efficacy of insulin boluses while also reducing patient burden and reducing the likelihood of manual errors.

Figure 5:
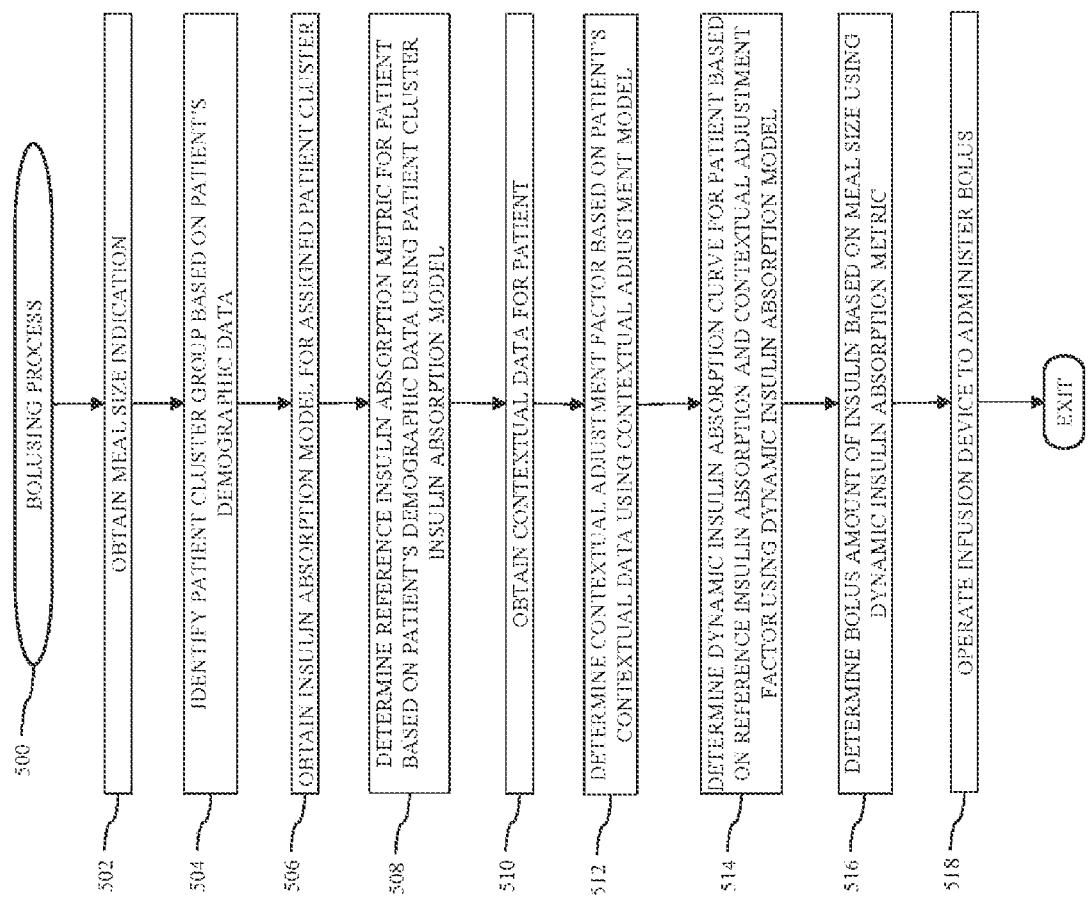
FIG. 5 is a flow diagram of an exemplary bolusing process suitable implementation in connection with an infusion device in one or more exemplary embodiments.

FIG. 5 depicts an exemplary embodiment of a bolusing process 500 that may be performed to determine and administer bolus dosages that are influenced by a dynamically determined insulin absorption metric. The various tasks performed in connection with the bolusing process 500 may be performed by hardware, firmware, software executed by processing circuitry, or any combination thereof. For illustrative purposes, the following description refers to elements mentioned above in connection with FIGS. 1-4. In practice, portions of the bolusing process 500 may be performed by different elements of an infusion system, such as, for example, an infusion device 102, 202, 402, a client computing device 106, 406, a remote computing device 108, 414, and/or a pump control system 220, 300. It should be appreciated that the bolusing process 500 may include any number of additional or alternative tasks, the tasks need not be performed in the illustrated order and/or the tasks may be performed concurrently, and/or the bolusing process 500 may be incorporated into a more comprehensive procedure or process having additional functionality not described in detail herein. Moreover, one or more of the tasks shown and described in the context of FIG. 5 could be omitted from a practical embodiment of the bolusing process 500 as long as the intended overall functionality remains intact.

In exemplary embodiments, bolusing process 500 is performed when a patient or other user manually initiates or interacts with a bolus wizard or other feature of the infusion device 102, 202, 402 or a client application 408 on the client device 106, 406 to configure and administer boluses (e.g., for contemporaneous meal events). The illustrated embodiment of the bolusing process 500 receives or otherwise obtains an indication of a meal size for the meal to be bolused (task 502). In this regard, the patient may interact with a bolus wizard feature of a particular application 308, 310, 408 used to administer meal boluses to input or otherwise provide an indication of an amount of carbohydrates or other information about the size or characteristics of a meal to be bolused for. For example, the client application 408 at the client device 406 may generate or otherwise provide a bolus wizard GUI display that includes one or more GUI elements that the patient can manipulate using client device 406 (e.g., user interface 428) to indicate the current meal size.

The bolusing process 500 identifies or otherwise determines a patient cluster group for the current patient using the patient's demographic data, retrieves or otherwise obtains an insulin absorption model associated with that identified patient cluster, and then calculates or otherwise determines a reference insulin absorption metric for the current patient as a function of a subset of the patient's demographic data using the insulin absorption model for the assigned patient cluster group (tasks 504, 506, 508). For example, as described in greater detail below in the context of FIG. 8, the remote server 414 may analyze the demographic data associated with different patients having data maintained in the database 416 to cluster or otherwise organize patients into different groups of similar patients based on their associated demographic data, for example, by the degree of similarities across different demographic attributes (e.g., age, race, gender, geographic region, socioeconomic status, profession, etc.) relative to other patients. Any suitable clustering technique could be used to divide patients into any number of different subsets or groups, which may be unique and mutually exclusive with respect to one another, such that each patient is only assigned to one cluster group. That said, it should be noted that the subject matter described herein is not limited to any particular type of clustering technique, any particular number of demographic attributes analyzed for the purposes of clustering, and/or any particular number or exclusivity of cluster groups. The demographic data associated with the current patient may then be analyzed to map or otherwise assign the current patient to one of the previously identified patient cluster groups, for example, by identifying the patient cluster group having representative demographic data associated therewith (e.g., the mean or median demographic data for patients assigned to the cluster) that is closest to the current patient's combination of demographic data. That said, other embodiments may assign patients to cluster groups categorically across one or more different categorical variables (e.g., gender).

For each patient cluster, the remote server 414 may analyze the historical glucose measurement data, historical insulin delivery data, and/or other historical data associated with the respective patients assigned to that respective cluster group to develop a model for calculating an insulin absorption metric for a patient belonging to that cluster group as a function of a subset of that patient's demographic data. For example, the remote server 414 may utilize a neural network or other machine learning or artificial intelligence techniques to determine which combination of demographic variables are correlated to or predictive of the insulin absorption rate from among patients assigned to the cluster group, and then determine a corresponding equation, function, or model for calculating an insulin absorption metric (e.g., an insulin absorption curve or other metric) as a function of those demographic variables. The remote server 414 may store or otherwise maintain the reference absorption model in the database 416 in association with the respective patient cluster group. In some embodiments, the remote server 414 utilizes the correlative subset of demographic variables associated with the current patient to calculate or otherwise determine a reference insulin absorption curve for the current patient using a reference insulin absorption curve model associated with the current patient's assigned patient cluster group. In other embodiments, the remote server 414 provides the reference insulin absorption curve model to the client device 406 or infusion device 402 for determination of the reference insulin absorption curve at the client device 406 or infusion device 402.

Still referring to FIG. 5, the bolusing process 500 also receives or otherwise obtains data indicative of the current contextual state for the patient and then calculates or otherwise determines a contextual adjustment factor as a function of the current patient context using a contextual adjustment model associated with the patient (tasks 510, 512). For example, a bolus wizard application 408 may monitor or otherwise obtain the patient's activity or event log data, meal data, auxiliary measurement data (e.g., from sensing arrangements 206, 208), the current time of day, the current day of the week, the current geographic location and/or the like to identify a set of variables that characterize or otherwise define the current contextual state of the patient. In this regard, the contextual variable values may collectively indicate whether the patient is engaged in or experiencing exercise, stress, menstruation, time of day and/or other conditions that may impact insulin absorption (e.g., day of the week (weekend versus weekday), geographic location (work versus home versus vacation/travel), etc.). The contextual variable values defining the current patient state are then input or otherwise provided to the patient's contextual adjustment model to determine a corresponding contextual adjustment factor that accounts for the likely impact of the current patient context on the patient's insulin absorption.

For example, a given patient, the remote server 414 may analyze the relationships between the patient's historical glucose measurement data, historical insulin delivery data, and historical event log data and/or other historical contextual data (or different prior instances of different patient contexts) to develop a model for calculating the likely effect on the patient's insulin absorption as a function of a subset of contextual variables. For example, the remote server 414 may utilize machine learning or artificial intelligence techniques to determine which combination of event log variables or parameters and other contextual variables or parameters are correlated to or predictive of changes to the patient's insulin absorption rate from among the patient's historical data, and then determine a corresponding equation, function, or model for calculating the likely change to the patient's insulin absorption as a function of those contextual variables. The remote server 414 may store or otherwise maintain the contextual adjustment model in the database 416 in association with the respective patient. In some embodiments, the remote server 414 provides the contextual adjustment model to the client device 406 or infusion device 402 associated with the patient for real-time determination of the contextual adjustment factor based on the current value or state of the contextual variables at the client device 406 or infusion device 402. That said, in other embodiments, data or information indicative of the current patient context may be uploaded or otherwise provided by the client device 406 or infusion device 402 to the remote server 414, which, in turn utilizes the contextual adjustment model to calculate or otherwise determine a contextual adjustment factor for the current patient context using the most recently uploaded contextual data.

Still referring to FIG. 5, after determining a contextual adjustment factor for the current patient context, the bolusing process 500 continues by calculating or otherwise determining a dynamic insulin absorption metric for the current patient context based on the current contextual adjustment factor for the current patient context and the reference insulin absorption metric for the patient using a dynamic insulin absorption model for the patient (task 514). In this regard, the current contextual adjustment factor for the current patient context and the reference insulin absorption metric for the patient are provided as inputs to an equation or function that calculates or otherwise determines a contextually adjusted insulin absorption metric. To obtain the dynamic insulin absorption model, the remote server 414 may retroactively apply the patient cluster reference absorption model and the patient's contextual adjustment model to the patient's historical data at or around prior bolus events to determine sets of reference insulin absorption metrics and contextual adjustment factors associated with those prior bolus events. Thereafter, the remote server 414 utilizes artificial intelligence or machine learning to analyze the relationships between the patient's historical glucose measurement data, historical insulin delivery data, and historical event log data (e.g., the relationships between bolus dosages, carbohydrate amounts, and glycemic response) and the respective sets reference insulin absorption metrics and contextual adjustment factors corresponding to the different bolus events to derive or otherwise develop a model for calculating the patient's insulin absorption as a function of the reference insulin absorption metric and the contextual adjustment factor. Similar to the other models, the remote server 414 may store or otherwise maintain the dynamic insulin absorption model in the database 416 in association with the respective patient or provide the dynamic insulin absorption model to the patient's associated client device 406 and/or infusion device 402.

In an exemplary embodiment, to determine sets of reference insulin absorption metrics, a physiological model equation for calculating the patient's glucose level as a function of the patient's historical glucose measurement data, historical insulin delivery data, and historical event log data and the insulin absorption metrics is determined by optimizing the weighting factors and/or relationships between input variables to minimize a cost function corresponding to the cumulative differences between the model-predicted (or simulated) glucose level and the patient's historical glucose measurement data. In this manner, the physiological model is utilized to derive a corresponding time series of historical IOB data for the patient that minimizes the cumulative differences between the model-predicted glucose level and the patient's historical glucose measurement data while reflecting the historical insulin delivery data. In this regard, the time series of historical IOB data and the weighting factors and/or other aspects of the physiological model may be iteratively adjusted until converging on an optimal solution. Thereafter, neural networks, artificial intelligence or other machine learning can be applied to analyze the relationships between the optimized historical IOB time series data, the historical contextual adjustment factor data, and the cluster-derived historical reference insulin absorption curves associated with the prior bolus events to arrive at a dynamic insulin absorption model for calculating or otherwise determining a dynamic insulin absorption curve (or metric or parameter corresponding thereto) as a function of the contextual adjustment factor and the cluster-derived insulin absorption curve (or metric or parameter corresponding thereto). In this regard, the optimized historical IOB time series data may be utilized to provide historical dynamic insulin absorption curves (or metrics or parameters corresponding thereto) that provide the respective outputs to be calculated as a function of the respective sets of historical contextual adjustment factors and cluster-derived historical reference insulin absorption curves.

Still referring to FIG. 5, after determining the dynamic insulin absorption metric that accounts for the current or real-time patient context and the patient's demographic data, the bolusing process 500 calculates or otherwise determines a bolus dosage of insulin to be delivered based on the input meal size using the dynamic insulin absorption metric and commanding, signaling, or otherwise operating the infusion device to administer the determined bolus dosage (tasks 516, 518). For example, an initial bolus dosage may be determined by the bolus wizard application 418 based on the amount of carbohydrates associated with the meal and the patient's carbohydrate ratio (e.g., by multiplying the amount of carbohydrates by the carbohydrate ratio). Thereafter, the bolus wizard application 408 may utilize the dynamic insulin absorption metric along with the patient's insulin sensitivity factor and current or recent glucose measurement to calculate or otherwise determine the current IOB and a predicted glycemic response for the patient with respect to time into the future assuming consumption of the meal and delivery of the bolus dosage. Based on the current IOB and the predicted glycemic response, as influenced by the dynamically-determined and context-sensitive insulin absorption metric, the bolus wizard application 408 may automatically adjust the bolus dosage amount to achieve the desired glycemic response or otherwise optimize the bolus (e.g., to maximize time in range, minimize probability of hyperglycemia and/or hypoglycemia, minimize insulin delivery, and/or the like). After the bolus dosage amount is determined, the command generation application 310 may be commanded, signaled, or otherwise instructed to operate the motor 232 of the infusion device 202 to deliver the calculated bolus dosage of insulin. In some embodiments, the calculated meal bolus dosage may be automatically administered; however, in other embodiments, a notification of the calculated meal bolus dosage may be generated or otherwise provided on a GUI display for review, modification, and/or confirmation by the patient. Such a GUI display may also include indication of the dynamic insulin absorption metric for review, modification, and/or confirmation. In this regard, some embodiments may allow the patient to override the bolusing process 500 and modify the dynamic insulin absorption metric.

Figure 6:
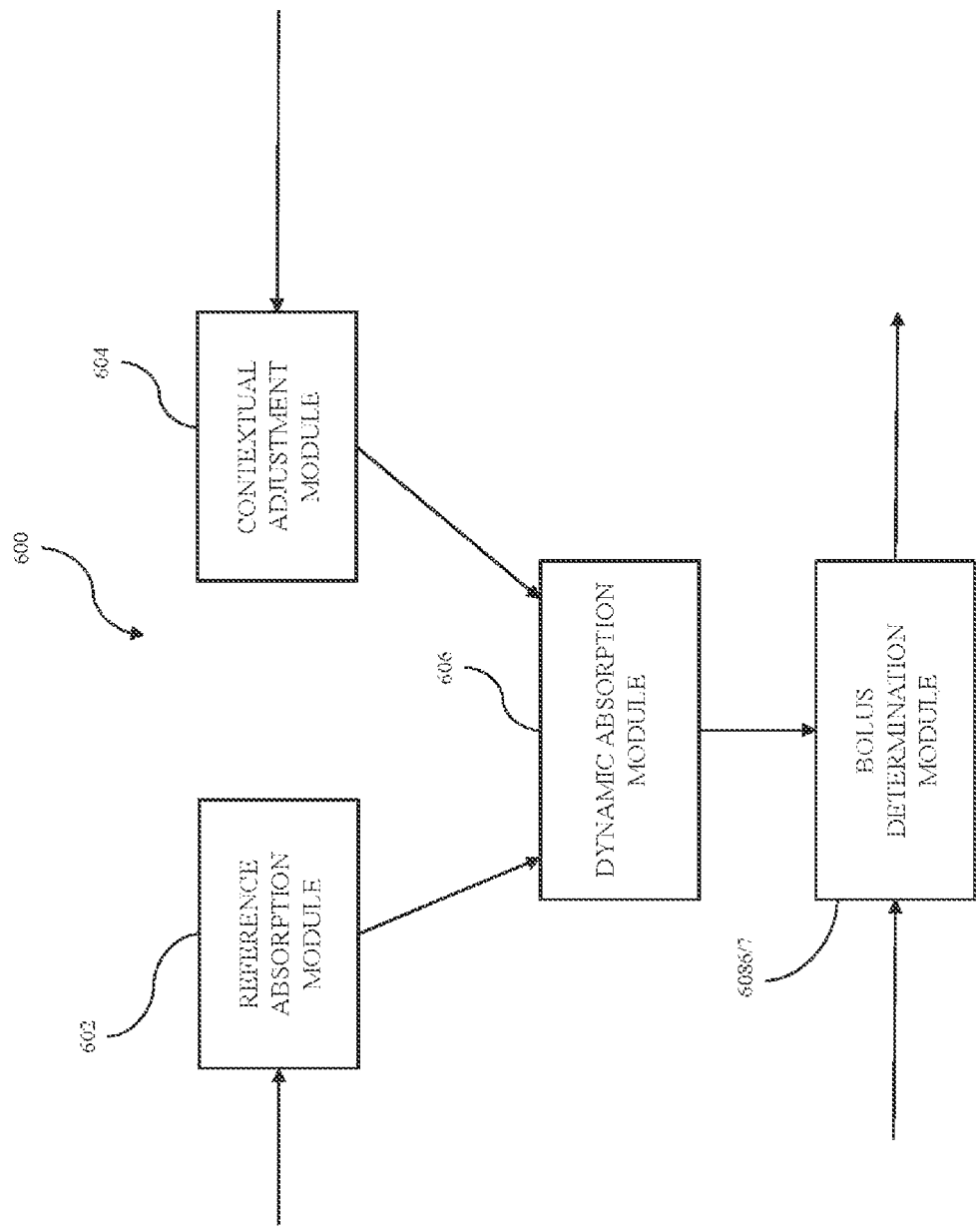
FIG. 6 depicts an exemplary embodiment of a dynamic bolusing system suitable for implementing the bolusing process of FIG. 5 in one or more exemplary embodiments.

FIG. 6 depicts an exemplary embodiment of a dynamic bolusing system 600 suitable for use in connection with the bolusing process 500 of FIG. 5, and suitable for implementation by a control system 220, 300 associated with an infusion device 202, 402 or another application 308, 310, 408 capable of determining bolus dosage amounts. The dynamic bolusing system 600 includes, without limitation, a reference absorption module 602, a contextual adjustment module 604, a dynamic absorption module 606, and a bolus determination module 608. It should be understood that FIG. 6 is a simplified representation of a dynamic bolusing system 600 for purposes of explanation and is not intended to limit the subject matter described herein in any way. Depending on the embodiment, the dynamic bolusing system 600 may be implemented using hardware, firmware, software executed by processing circuitry, or any combination thereof.

The reference absorption module 602 generally represents the component of the dynamic bolusing system 600 that is configured to receive or otherwise obtain the patient's demographic data and apply the reference absorption model for the patient's assigned patient cluster to calculate or otherwise determine a reference absorption metric (R0) for the patient based on the patient's demographic data. For example, the reference absorption module 602 may output or otherwise provide a reference insulin absorption curve that reflects the patient's demographic data using a reference absorption model derived from patients having similar demographic characteristics.

The contextual adjustment module 604 generally represents the component of the dynamic bolusing system 600 that is configured to receive or otherwise obtain the most recent or real-time contextual data for the patient (e.g., from auxiliary sensing arrangements 206, 208, the patient's event log, and/or the like) that characterize or otherwise define the current contextual state for the patient and apply the patient's contextual adjustment model to the current contextual state variable values to calculate or otherwise determine a contextual adjustment factor (p) for the patient based on the patient's current context. In this regard, the contextual adjustment factor represents the degree to which the patient's insulin absorption rate is likely to increase or decrease given the current context based on the patient's historical insulin absorption, which may be derived based on relationships between the patient's historical meal, insulin delivery, and glucose measurement data, as described herein.

The dynamic absorption module 606 generally represents the component of the dynamic bolusing system 600 that is configured to receive or otherwise obtain the reference absorption metric (R0) for the patient from the reference absorption module 602 and the contextual adjustment factor (p) for the patient from the contextual adjustment module 604, and then calculate or otherwise determine a dynamic absorption metric (R) for the patient as a function of the reference absorption metric (R0) and the contextual adjustment factor (p) (e.g., R=g(R0, p), where the equation g( ) is derived from the patient's historical data, as described herein). For example, the dynamic absorption module 606 may calculate or otherwise determine a contextually-adjusted insulin absorption curve for the patient based on a reference insulin absorption curve provided by the reference absorption module 602 by applying the contextual adjustment factor (p) provided by the contextual adjustment module 604 in accordance with an equation, function, or model derived by applying artificial intelligence or machine learning to the relationships between the patient's historical insulin delivery data, historical sensor glucose measurement data, historical meal data, and corresponding sets of retroactively determined contextual adjustment factors and/or reference insulin absorption curves.

Figure 7:
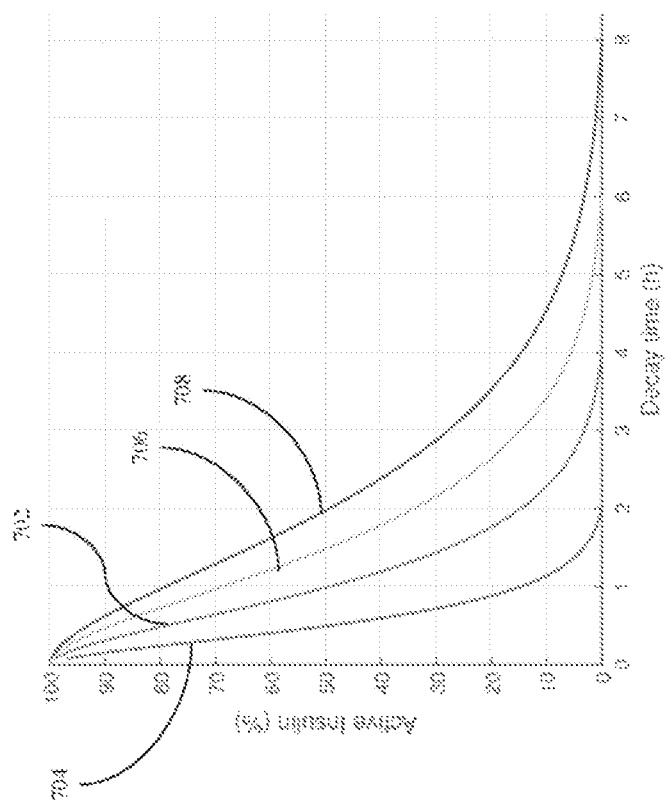
FIG. 7 depicts a graph of absorption curves suitable for use in the dynamic bolusing system of FIG. 6 in connection with the bolusing process of FIG. 5 in one or more exemplary embodiments.

For example, FIG. 7 depicts a graph of exemplary insulin absorption curves 702, 704, 706, 708 that may be output by the dynamic absorption module 606 depending on the contextual adjustment factor. For example, the reference absorption module 602 may output or otherwise provide indication that the reference insulin absorption curve for that patient has a four-hour decay period (e.g., curve 702) for one hundred percent of bolus insulin delivered to be absorbed or metabolized by the patient. When the real-time contextual adjustment factor provided by the contextual adjustment module 604 indicates an increased insulin absorption rate by a factor of two for the current patient context, the dynamic absorption module 606 may dynamically determine an adjusted insulin absorption curve having a two hour decay period (e.g., curve 704). Conversely, when the real-time contextual adjustment factor provided by the contextual adjustment module 604 indicates a decreased insulin absorption rate by a factor of two for the current patient context, the dynamic absorption module 606 may dynamically determine an adjusted insulin absorption curve having an eight hour decay period (e.g., curve 708). In this regard, the dynamic absorption module 606 may output indicia corresponding to a different one of the curves 702, 704, 706, 708 depending on the current contextual adjustment factor.

Referring again to FIG. 6, the bolus determination module 608 generally represents the component of the dynamic bolusing system 600 that is configured to receive or otherwise obtain the contextually adjusted insulin absorption metric for purposes of determining a bolus amount. In this regard, in addition to the contextually-adjusted insulin absorption metric provided by the dynamic absorption module 606, the bolus determination module 608 may also receive or otherwise obtain the current or most recent sensor glucose measurement values for the patient, the amount of carbohydrates or other indicia of the meal size to be bolused for, and the like. As described above, the bolus determination module 608 utilizes the patient's contextually-adjusted insulin absorption curve in connection with the patient's carbohydrate ratio, insulin sensitivity factor, current glucose measurement value (and potentially the trend associated therewith) to determine a bolus dosage of insulin to be delivered that accounts for the anticipated or expected glycemic response of the patient in the future. In this regard, the particular insulin absorption curve 702, 704, 706, 708 output by the dynamic absorption module 606 influences the insulin on board calculations and the resulting simulated future glucose levels determined by the bolus determination module 608. Thus, by accounting for the current patient context along with the patient's demographic data, the accuracy or reliability of the simulated future glucose levels may be improved, thereby improving the efficacy of the resulting bolus dosage and reducing the likelihood of postprandial hyperglycemia, hypoglycemia, or other glucose excursions. The resulting bolus dosage determined by the bolus determination module 608 may be presented or otherwise depicted to the patient or other user for verification or confirmation before providing a bolus dosage command to the pump control system 220, 300 for autonomously operating an actuation arrangement 214, 232 of the infusion device 202, 402 to achieve the commanded dosage.

For the sake of brevity, conventional techniques related to glucose sensing and/or monitoring, sensor calibration and/or compensation, bolusing, machine learning and/or artificial intelligence, clustering, pharmodynamic modeling, and other functional aspects of the subject matter may not be described in detail herein. In addition, certain terminology may also be used in the herein for the purpose of reference only, and thus is not intended to be limiting. For example, terms such as "first," "second," and other such numerical terms referring to structures do not imply a sequence or order unless clearly indicated by the context. The foregoing description may also refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:

1. A processor-implemented method comprising:
   identifying a reference insulin absorption curve for a patient based on demographic data of the patient;
   identifying a contextual adjustment factor based on current contextual information for the patient;
   obtaining an adjusted insulin absorption curve based on the reference insulin absorption curve and the contextual adjustment factor; and
   causing insulin delivery to the patient based on the adjusted insulin absorption curve.

2. The method of claim 1, wherein obtaining the adjusted insulin absorption curve comprises:
   providing the reference insulin absorption curve and the contextual adjustment factor as inputs to an insulin absorption model; and
   obtaining the adjusted insulin absorption curve based on the insulin absorption model.

3. The method of claim 2, wherein the insulin absorption model is derived based on application of machine learning to analyze relationships between historical insulin on board (IOB) time series data, historical contextual adjustment factor data, and historical reference insulin absorption curves associated with prior bolus events.

4. The method of claim 3, wherein the historical IOB time series data is optimized based on minimizing cumulative differences between simulated glucose levels and historical glucose measurement data of the patient.

5. The method of claim 1, wherein the reference insulin absorption curve is associated with a patient cluster corresponding to the patient's demographic data.

6. The method of claim 1, wherein the contextual adjustment factor is determined based on providing the current contextual information as input to a model for predicting how the current contextual information will affect an insulin absorption rate of the patient, and identifying the contextual adjustment factor based on the model.

7. The method of claim 1, wherein the current contextual information includes at least one of a group comprising a time of day, a day of the week, a geographic location, and an activity level of the patient.

8. A system comprising:
   one or more processors; and
   one or more processor-readable storage media storing instructions which, when executed by the one or more processors, cause performance of:
   identifying a reference insulin absorption curve for a patient based on demographic data of the patient;
   identifying a contextual adjustment factor based on current contextual information for the patient;
   obtaining an adjusted insulin absorption curve based on the reference insulin absorption curve and the contextual adjustment factor; and
   causing insulin delivery to the patient based on the adjusted insulin absorption curve.

9. The system of claim 8, wherein obtaining the adjusted insulin absorption curve comprises:
   providing the reference insulin absorption curve and the contextual adjustment factor as inputs to an insulin absorption model; and
   obtaining the adjusted insulin absorption curve based on the insulin absorption model.

10. The system of claim 9, wherein the insulin absorption model is derived based on application of machine learning to analyze relationships between historical insulin on board (IOB) time series data, historical contextual adjustment factor data, and historical reference insulin absorption curves associated with prior bolus events.

11. The system of claim 10, wherein the historical IOB time series data is optimized based on minimizing cumulative differences between simulated glucose levels and historical glucose measurement data of the patient.

12. The system of claim 8, wherein the reference insulin absorption curve is associated with a patient cluster corresponding to the patient's demographic data.

13. The system of claim 8, wherein the contextual adjustment factor is determined based on providing the current contextual information as input to a model for predicting how the current contextual information will affect an insulin absorption rate of the patient, and identifying the contextual adjustment factor based on the model.

14. The system of claim 8, wherein the current contextual information includes at least one of a group comprising a time of day, a day of the week, a geographic location, and an activity level of the patient.

15. One or more processor-readable storage media storing instructions which, when executed by one or more processors, cause performance of:
   identifying a reference insulin absorption curve for a patient based on demographic data of the patient;
   identifying a contextual adjustment factor based on current contextual information for the patient;
   obtaining an adjusted insulin absorption curve based on the reference insulin absorption curve and the contextual adjustment factor; and
   causing insulin delivery to the patient based on the adjusted insulin absorption curve.

16. The one or more processor-readable storage media of claim 15, wherein obtaining the adjusted insulin absorption curve comprises:

providing the reference insulin absorption curve and the contextual adjustment factor as inputs to an insulin absorption model; and obtaining the adjusted insulin absorption curve based on the insulin absorption model.

17. The one or more processor-readable storage media of claim 16, wherein the insulin absorption model is derived based on application of machine learning to analyze relationships between historical insulin on board (IOB) time series data, historical contextual adjustment factor data, and historical reference insulin absorption curves associated with prior bolus events.

18. The one or more processor-readable storage media of claim 17, wherein the historical IOB time series data is optimized based on minimizing cumulative differences between simulated glucose levels and historical glucose measurement data of the patient.

19. The one or more processor-readable storage media of claim 15, wherein the reference insulin absorption curve is associated with a patient cluster corresponding to the patient's demographic data.

20. The one or more processor-readable storage media of claim 15, wherein the contextual adjustment factor is determined based on providing the current contextual information as input to a model for predicting how the current contextual information will affect an insulin absorption rate of the patient, and identifying the contextual adjustment factor based on the model.

* * * * *